(12) United States Patent
Boksberger et al.

(10) Patent No.: US 6,385,482 B1
(45) Date of Patent: May 7, 2002

(54) DEVICE AND PROCESS FOR DETERMINING POSITION

(75) Inventors: Hans Boksberger, Oberbozberg; Urs Greuter, Baden; Stefan Kirsch, Wurenlingen; Paul Seiler, Villigen; Christian Schilling, Wurenlingen, all of (CH)

(73) Assignee: Mednetix AG, Villigen (CH)

( * ) Notice: Subject to any disclaimer, the term of this patent is extended or adjusted under 35 U.S.C. 154(b) by 0 days.

(21) Appl. No.: 09/161,395

(22) Filed: Sep. 28, 1998

Related U.S. Application Data (63) Continuation of application No. PCT/CH97/00132, filed on Mar. 27, 1997.

(30) Foreign Application Priority Data

Mar. 27, 1996 (CH) ................................................ 797/96

(51) Int. Cl.[7] ................................................ A61B 5/05
(52) U.S. Cl. .................. 600/424; 324/207.13; 324/260
(58) Field of Search ............................... 600/407, 409, 600/424; 128/899; 324/244, 247, 248, 260, 207.11, 207.15

(56) References Cited

U.S. PATENT DOCUMENTS

| | | | |
|---|---|---|---|
| 4,317,078 A | | 2/1982 | Weed et al. |
| 4,995,395 A | * | 2/1991 | Ilmoniemi et al. |
| 5,122,744 A | * | 6/1992 | Koch ........................... 324/248 |
| 5,134,370 A | * | 7/1992 | Jefferts et al. ............... 324/247 |
| 5,313,944 A | * | 5/1994 | Crowley et al. |
| 5,833,608 A | * | 11/1998 | Acker ......................... 600/409 |
| 5,868,673 A | * | 2/1999 | Vesely ........................ 600/407 |

FOREIGN PATENT DOCUMENTS

| | | |
|---|---|---|
| EP | 0 091 577 A1 | 10/1983 |
| EP | 0 364 045 A1 | 4/1990 |
| EP | 0 425 319 A2 | 5/1991 |
| WO | 94/04938 | 3/1994 |

OTHER PUBLICATIONS

International Search Report dated Jul. 17, 1997.

* cited by examiner

*Primary Examiner*—Marvin M. Lateef
*Assistant Examiner*—Shawna J Shaw
(74) *Attorney, Agent, or Firm*—Burns, Doane, Swecker & Mathis, L.L.P.

(57) ABSTRACT

A device for determining the position of objects (T) inside a space (P), in particular for locating a tumor inside a human body. At least one emitter unit (SE) and at least one receiver unit (S11, . . . S22) are provided and, in a first embodiment, the emitter unit(s) (SE) are located inside and/or as close as possible to the object (T) under observation and the receiver units(s) (S11, . . . S22) are located preferably outside the space (P). In a second embodiment, the receiver unit(s) (SE) are located inside and/or as close as possible to the object (T) under observation and the emitter unit(s) (S11, . . . S22) are located preferably outside the space (P).

32 Claims, 5 Drawing Sheets

DEVICE AND PROCESS FOR DETERMINING POSITION

This application is a continuation of PCT Application No. PCT/CH97/00132 filed on Mar. 27, 1997, which designated the United States.

The invention at hand relates to a device according to the preamble of claim 1, its use, a process according to the preamble of claim 15, as well as an application of the process.

BACKGROUND OF THE INVENTION

Information regarding the position of an object are of utmost importance for many technical and medical processes. While in medicine the position of individual tissue parts —e.g., of a tumor to be irradiated in order to be destroyed or in order to limit its growth—must be determined, the determination of position for input into a computer system, e.g., for "cyber space" applications, is of general importance. Such a position determination or position input unit also is referred to in these applications as, e.g., a three-dimensional mouse. Reference is made in this context to publications U.S. Pat. No. 4, 737, 794, U.S. Pat. No. 4, 945, 305 and U.S. Pat. No. 5, 453, 686.

A medical application is—as mentioned—the treatment of tumors in the human body, whereby the tumor is irradiated with photon or, in special cases, with proton beams. The objective of such a radiation treatment is that only the tissue part forming the tumor is irradiated. Damage to the tissue surrounding the tumor is supposed to be as little as possible. Attempts to achieve this requirement are made by adapting the dose distribution of the applied beam as accurately as possible to the tumor volume or limiting it to the tumor site.

Different methods are known both for photon and proton. irradiation, whereby in some cases significant differences in quality among the various methods exist. With all of these known methods it is presupposed that—while preventing damage to healthy tissue—a tumor position, once diagnosed, will remain constant over the treatment period.

In some cases, remarkable successes were achieved in the treatment of stationary tumors. In particular, the treatment of eye background melanomas with proton beams was found to be extremely successful.

In contrast, tumors in the thoracic and abdominal area are generally not stationary. Rather, their position constantly changes due to natural movement processes, e.g., respiration, heart contractions, peristaltics, etc.

If similar successful treatment results are to be achieved as those in stationary tumors, the tumor location must be accurately known during treatment.

For this reason, a paper by K. Ohara et al., titled "Irradiation Synchronized With Respiration Gate" (International Journal on Radiation Oncology Biology Physics, 1989, Vol. 17, pp. 853–857), suggested a real-time simulation of the tumor position, whereby the basis of the simulation was the deformation of the body surface, in particular the deformation due to respiratory movement. However, this method is characterized by inaccuracies, since it represents, on the one hand, not a direct measurement of the tumor position, but only an indirect measurement, and, on the other hand, does not take into account the additional factors determining position—such as heart contraction and intestinal peristaltics.

SUMMARY OF THE INVENTION

The invention on hand is therefore based on the objective of describing a device which makes it possible to determine the position of objects at all times.

This objective is realized by the means described in the characterizing part of claim 1. Advantageous embodiments of the invention, its use, a process, as well as an application of the process, are described in further claims.

By using the device according to the invention, the position of an object in space can be determined with extreme accuracy. The position also can be determined without any direct connection to the object.

If a miniaturized, signal-transmitting emitter unit is attached to the tumor or to a tissue part near the tumor, it is then possible by receiving these signals outside the body through receiver units to exactly calculate the tumor position at any time. Analogously, the position can also be determined by placing the receiving unit inside or near the tumor, and the emitting unit(s) outside the body. The latter arrangement has the additional advantage that the body is exposed to a lesser transmission power and thus to a lower thermal stress than is the case with the method mentioned first. Also, the transmission of the signals measured at the object, i.e., the tumor, towards the outside, as in the last mentioned arrangement, is much simpler, since a lower transmission power must be made available for this transmission than with the first method.

In medical use, the unit positioned near the object, i.e., the tumor, is implanted surgically in the patient's body, if this is necessary. The first arrangement requires energy for emitting signals through the emitter unit, this energy being transmitted either via an external field to the emitter unit or via a wire connection between a generator unit and the emitter unit. In another embodiment of the invention, the emitter unit has its own energy supply which is therefore implanted along with it.

In the second arrangement, the above statements apply analogously, i.e., the signals received by the receiver unit(s) are transmitted via wire connections towards the outside. But in this form of realization—as mentioned—less energy is required for transmitting the measuring signals.

BRIEF DESCRIPTION OF THE DRAWINGS

The invention is described below in the form of an example in reference to drawings.

DETAILED DESCRIPTION OF THE INVENTION

Figure 1:
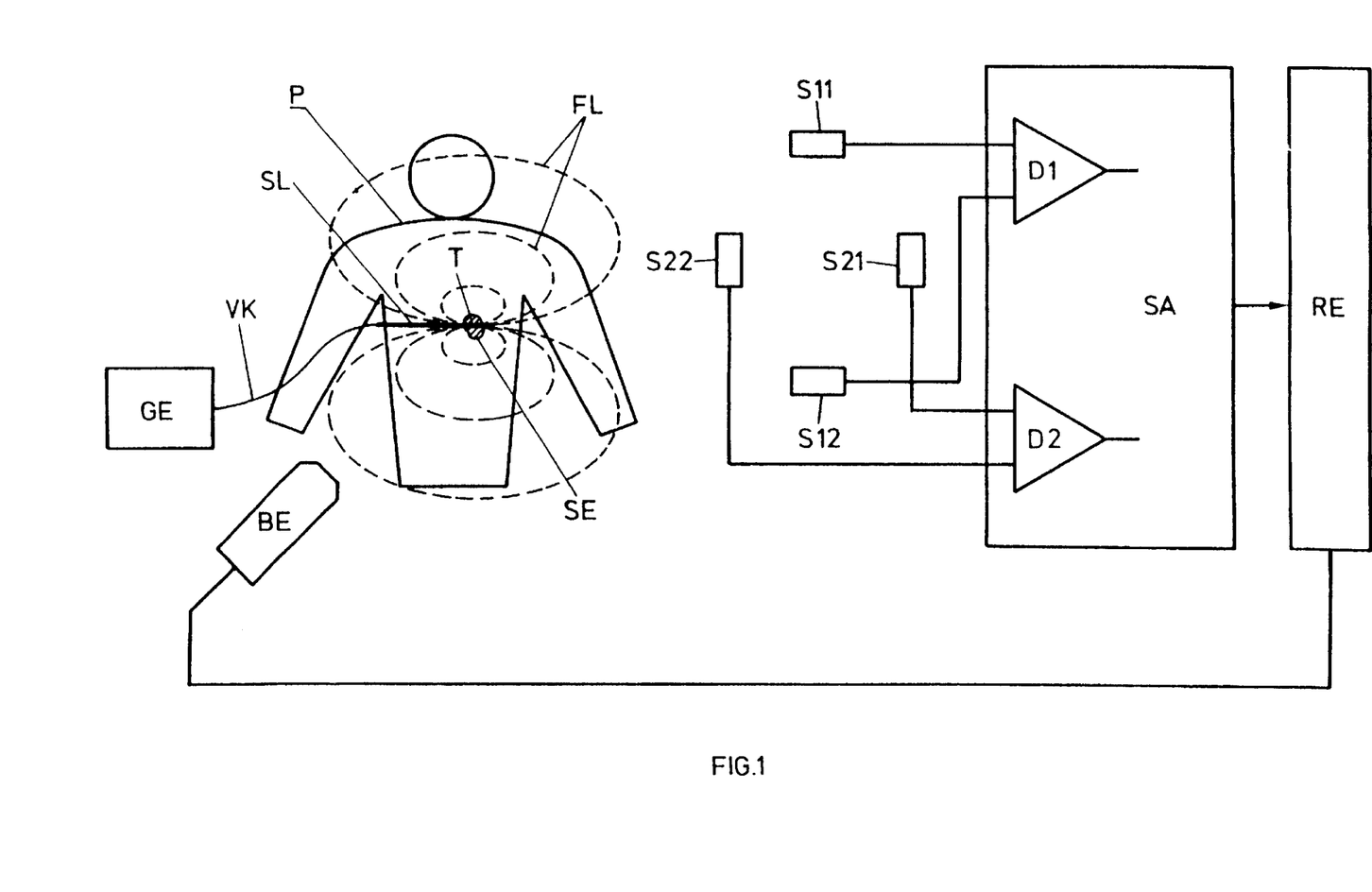
FIG. 1 shows a simplified function schematic of the device according to the invention.

FIG. 1 shows a human body P of a patient to be treated with the device according to the invention. The device according to the invention hereby consists of an emitter unit SE, a generator unit GE, a tube SL, receiver units S11 to S 22, a signal conditioning unit SA, a computation unit RE, and an irradiation unit BE.

As mentioned in the beginning, knowledge of the exact position of a tissue part T to be irradiated, e.g., a tumor, is the absolutely necessary condition for maximum protection of the healthy tissue adjoining the tumor. In order to determine position in this way, the invention provides that the miniaturized emitter unit SE is positioned as close as possible to the tumor, preferably immediately at it, so that the emitter unit SE, if possible, takes part in all movements which the tissue part T to be treated undergoes.

One possibility of positioning the emitter unit SE at the desired site in the body is the use of a hollow puncture needle with which the tube SL is passed from the body surface to the tissue part T. The emitter unit SE is brought through this tube SL into the tissue part T or near the tissue part T.

If the tissue part T to be irradiated is located on the body surface or near a natural body cavity, the emitter unit SE naturally must be fixed on the body surface or the emitter unit must be, if possible, inserted through a natural body opening into the respective body cavity without having. to penetrate tissue, e.g., when a hollow puncture needle is used.

If the position determination according to the invention is used to enable the radiation treatment of a tissue part T, e.g., a tumor, the computation unit RE is in effective connection with the radiation unit BE. This makes it possible for the radiation unit BE to act precisely on the tissue part T, whereby two principal possibilities of the radiation process are conceivable: On the one hand, it is conceivable that a target area in which the beams are unfolding their full effect tracks the moving and irradiated tissue part T, or, on the other hand, the irradiation is performed only when the tissue part T is located in the target area that has been given as a stationary area.

In the already mentioned embodiment of the invention shown in FIG. 1, the emitter unit SE is supplied with energy via a connecting cable VK that passes through the tube SL and which is connected on one side to the generator unit GE and on the other side to the emitter unit SE.

It would, however, also be conceivable that the emitter unit SE is provided with an energy supply, e.g., in; the form of a battery, or that the emitter unit SE is excited by an electromagnetic field generated by the generator unit GE. These two embodiments have the advantage that no connecting cables VK are necessary between the generator unit GE and the emitter unit SE, so that a field radiated by the emitter unit SE and used for determining position is not interfered with. In addition, the emitter unit SE can be left in the body between individual treatments. But the disadvantage is the resulting larger emitter unit SE—in particular in the embodiment with the energy supply integrated in the emitter unit SE—which can be an impairment, particularly in the case of an implantation in the body.

The emitter unit SE is used to build up an electromagnetic field, shown in FIG. 1 by the separate field lines FL, which can be received by the receiver units S11 to S22 that are preferably arranged outside the body P. Although a human body P represents a very heterogeneous medium in respect to the propagation properties of electromagnetic waves in the various tissues, the influence of a magnetic field penetrating through a body P is negligible. For this reason, the preferred embodiment of the emitter unit SE placed in the body P consists of a miniaturized coil, whereby a magnetic field originating from this coil corresponds to a magnetic dipole. If the magnetic moment and the position of a dipole in space are known, the intensity of the magnetic field in each point in space can be calculated, whereby the values for the magnetic field strength are clearly determined by the three Cartesian coordinates x, y, z, the polar angle $\phi$, and the azimuth $\theta$ of the dipole. The magnetic moment of a dipole can be calculated or can be determined with suitable measurements.

The position of the dipole in space, as required in the application at hand, represents the inverse problem, i.e., the position of the dipole is determined based on the measurements of the field intensities of the field radiated from the dipole.

A complete determination of the position requires knowledge of the magnetic moment of the emitter unit SE or the emitting coil contained in the emitter unit SE, and the measurement of at least five linear, independent gradients of its magnetic field.

A possible method for determining the position of a magnetic dipole in space is described in the paper by W.M. Wynn et al., titled "Advanced Superconducting Gradiometer/Magnetometer Arrays and a Novel Signal Processing Technique" (IEEE Transactions of Magnetics, Vol. MAG-11, No. 2, March 1975, pp. 701–707). However, this known method for determining position presumes a dipole with unknown magnetic moment. For this reason, another component of the magnetic field must be measured in addition to the field gradients.

When applying this method to the teaching according to the invention, the magnetic moment can be obtained, however, in a measurement independent from the measurements for position determination, i.e., the field components need not be measured during the position determination.

The receiver units S11 to S22 have been provided in order to measure the field gradients, whereby two each of these receiver units, i.e., S11 and S12 or S21 and S22, are used to determine a field gradient. For reason of simplicity, FIG. 1 shows only the four receiving units S11 to S22. In fact, a total of ten receiving units are necessary so that the five variables x, z, y, $\phi$, and $\theta$ can be clearly determined. To check the measured value, it is, however, also provided that more than ten receiving units can be used, so that redundant information is obtained, based on which the measuring accuracy can be evaluated.

It is preferred that induction coils are used as receiver unit S11 to S22. The induction coils integrate the magnetic flux within their volume. The mean magnetic intensity in the coil volume then can be determined from this magnetic flux. But for the purpose of position determination, the field intensity in a single point in space is of interest.

The publication titled "Experimental Methods in Magnetism" by E. P. Wohlfarth (Volume 2, Chapter 1, pp. 2–7) says that when the coil dimensions are selected in a suitable manner, the measuring value supplied by the coil corresponds to the value of the magnetic field intensity, i.e., in the coil center, with only slight differences. This can be expected especially then when the ratio of length to diameter of the used induction coil is calculated according to the following formula:

$$\frac{\zeta}{\rho_2} = \frac{3}{\sqrt{20}} \cdot \sqrt{\frac{1-\gamma^2}{1-\gamma^3}}$$

whereby:

$$\gamma = \frac{\rho_1}{\rho_2}$$

and $\rho_1$, $\rho_2$ is the inside or respectively outside diameter of the induction coil. It was recently found that—if $\gamma<0.3$ —a fraction of the fourth order is smaller than $2\times10^{-3}$ and thus exerts a smaller influence than the magnetic induction $B_2$ along the symmetry axis of the induction coil.

As was already mentioned, two each of the receiver units S11 to S22 are switched together in order to determine the gradients of the magnetic field. For this purpose, the signal conditioning unit SA is provided with application, units D1 ad D2, each of which has two inputs, whereby at each input.

a receiver unit S11 to S22 or an induction coil is connected. It is again pointed out that, for a position determination in space, a correspondingly higher number of amplification units must be provided than is shown in FIG. 1, because FIG. 1, for reason of clarity, shows only two amplification units D1 and D2 and only four receiver units S11 to S22.

In the amplification units D1 and D2, the magnetic field difference of the two signal values present at these inputs is formed. This magnetic field difference is considered to be approximately equal to the gradient of the magnetic field.

Because of miniaturization, in particular of the emitter unit SE which is constructed as a coil, the generated magnetic field intensity is very small. Because of this, other magnetic field sources, such as do occur in spaces that are not specifically magnetically shielded, represent a problem. For this reason, a narrow-band filtration and/or a phase-sensitive amplification of the signal values obtained in the amplification units D1 and D2 is performed in the signal conditioning unit SA. This eliminates a large part of undesired signal portions, including noise. In addition, the formation of differentials in the amplification units D1 and D2 which are needed for determining the gradients of the magnetic field also help to reduce interfering influences.

The induction coils must be wound in a very homogenous and reproducible manner so that it is possible to accurately deduce the magnetic field intensity from the voltage induced in the coil. The homogeneity and reproducibility are extremely hard to achieve with traditional windings made from round copper wire. For this reason, two additional possibilities for realizing induction coils in which said disadvantages are prevented are suggested below.

First, an explanation is given of the device already explained at the beginning, which differs from the one first mentioned in that emitter and receiver units are interchanged. As a result a differential field is generated in that a current now flows through the coils, originally connected to measure a field gradient. This means that in this version of the embodiment the receiver unit or receiver units are located in or near object T—i.e., the tumor—and the emitter unit or emitter units are located outside of space K—i.e., the body. This embodiment version has the advantage that the emitter units located outside the body may have higher performance limits than in the first mentioned version. This results in a significantly better signal-to-noise ratio in the receiver unit, so that the requirements regarding the computation unit for processing the measuring signals are lower, and the measuring results become more accurate. In addition, the receiver unit placed at the object requires much lower quantities of energy for transmitting the measuring signals towards the outside, so that in most cases a receiver unit that is battery-based or based on a transponder principle is sufficient for this.

In order to improve the accuracy of the measuring signals further, several calibration coils with known positions are provided, based on which the interference values used for correction during the position determination can be determined.

In this second version of the embodiment, both a time and a frequency multiplexing process can be used for position determination. In the time multiplexing process, only one emitter unit is sending in each case—if a differential field is sent, the two corresponding emitter units S11 and S22 or S21 and S22—within a defined period of time. In contrast, in the frequency multiplexing process, all emitter units are sending at the same time, but with defined and different frequencies.

In the previously mentioned second embodiment of the invention, the configuration shown in FIG. 1 was presumed, whereby emission and receiving site were interchanged. Also conceivable would be an embodiment version in which the receiver unit SE is provided, e.g., with two coils used to measure either absolute values or field gradients. The corresponding is true for emitter units S11 to S22, each of which can be constructed either as a coil or as a pair of coils.

In order to determine the exact position, reference is made to the paper by S. Kirsch et al. titled "Real Time Tracking of Tumor Positions for Precision Irradiation" (Proceedings of the Second Symposium on Hadrontherapy, Sep. 9–13, 1996).

Figure 2A:
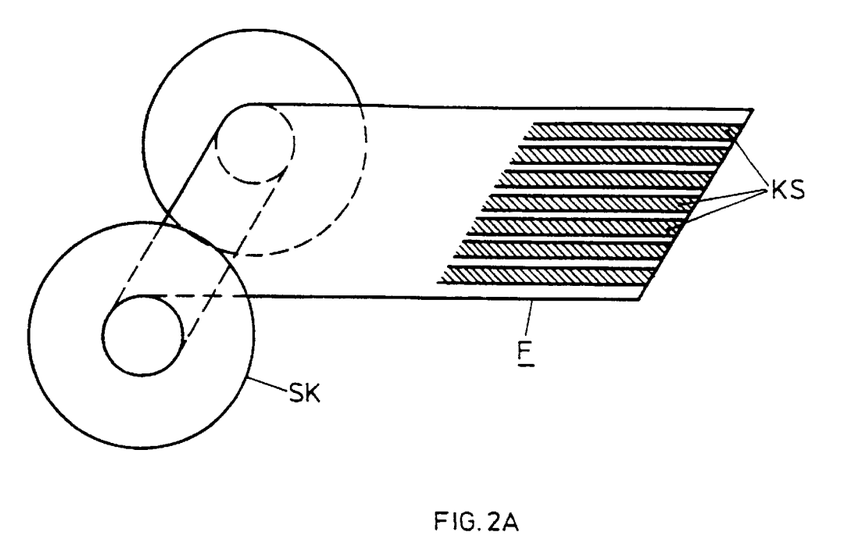
FIG. 2 shows the structure of an induction coil used as a receiver unit in the device according to the invention.
Figure 2B:
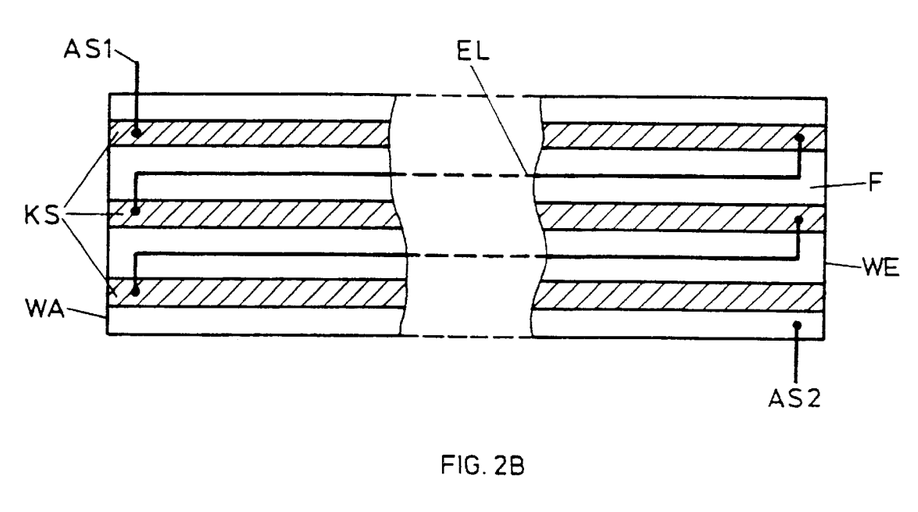

The following considers two further possibilities for realizing induction coils which make it possible to determine the voltages induced into the coils with a high degree of accuracy:

A first embodiment of the induction coil is shown in FIG. 2, whereby a foil F coated with parallel copper strips KS is used in place of a wire. The foil width corresponds to the desired winding length and thus to the length of a coil body SK to be provided with a winding. The foil F is wound, as shown in FIG. 2A, directly onto the coil body SK, whereby the entire wire layer corresponds to a standard induction coil of a foil layer. FIG. 2B shows how the parallel copper strips KS are connected with each other via an electrical connecting line EL. Hereby the end of a copper strip KS located in each case at the winding start WA must be connected to an end of the copper strip KS located at the winding end WE, something which requires a relatively complicated connection technique.

For the case in which only the differential signal of two induction coils is required, the just explained induction coil was therefore improved so that the use of the above mentioned connection technique can be avoided. As mentioned, only the differential signal of two induction coils is of interest for the application at hand (gradiometer), i.e., the measuring of field gradients. Based on this limitation, the winding thus can be simplified to this effect by producing both induction coils from the same foil F. This is shown with the help of FIG. 2C which shows that the foil F is folded twice at a right angle at the winding start WA. Furthermore, both induction coils are wound parallel onto the same coil body. This is achieved in that the same copper strip is passed once from the outside to the inside, and for the second induction coil from the inside to the outside. This induces a signal in the first induction coil, with reverse polarity, also into the second induction coil, so that equal signals compensate each other. From this results that at the connecting points AS1 and AS2 in the embodiment shown in FIG. 2C only the differential signal is present. The amplification units D1 and D2 explained in reference to FIG. 1 and constructed as differential amplifiers are no longer needed here.

Figure 2C:
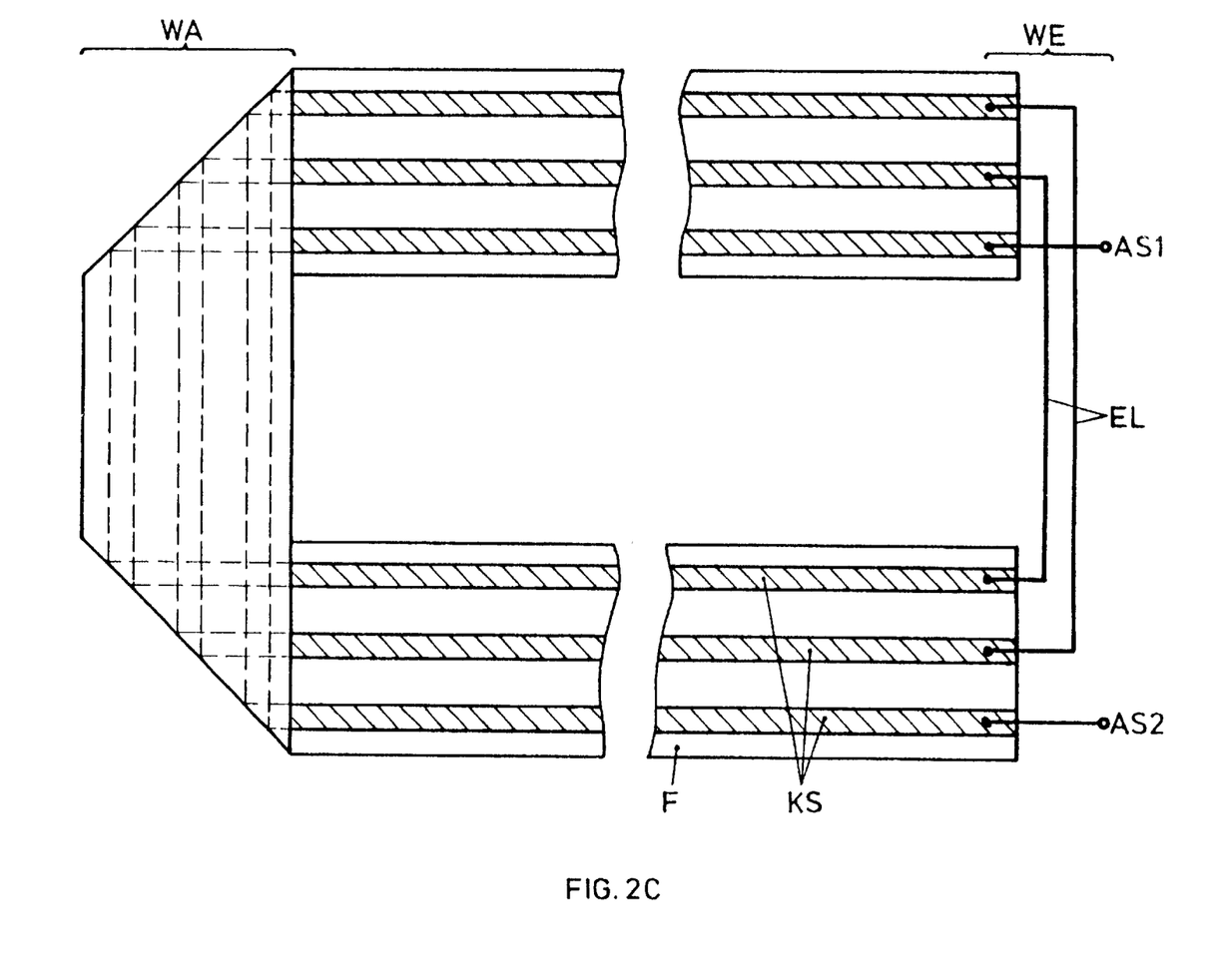
Figure 3A:
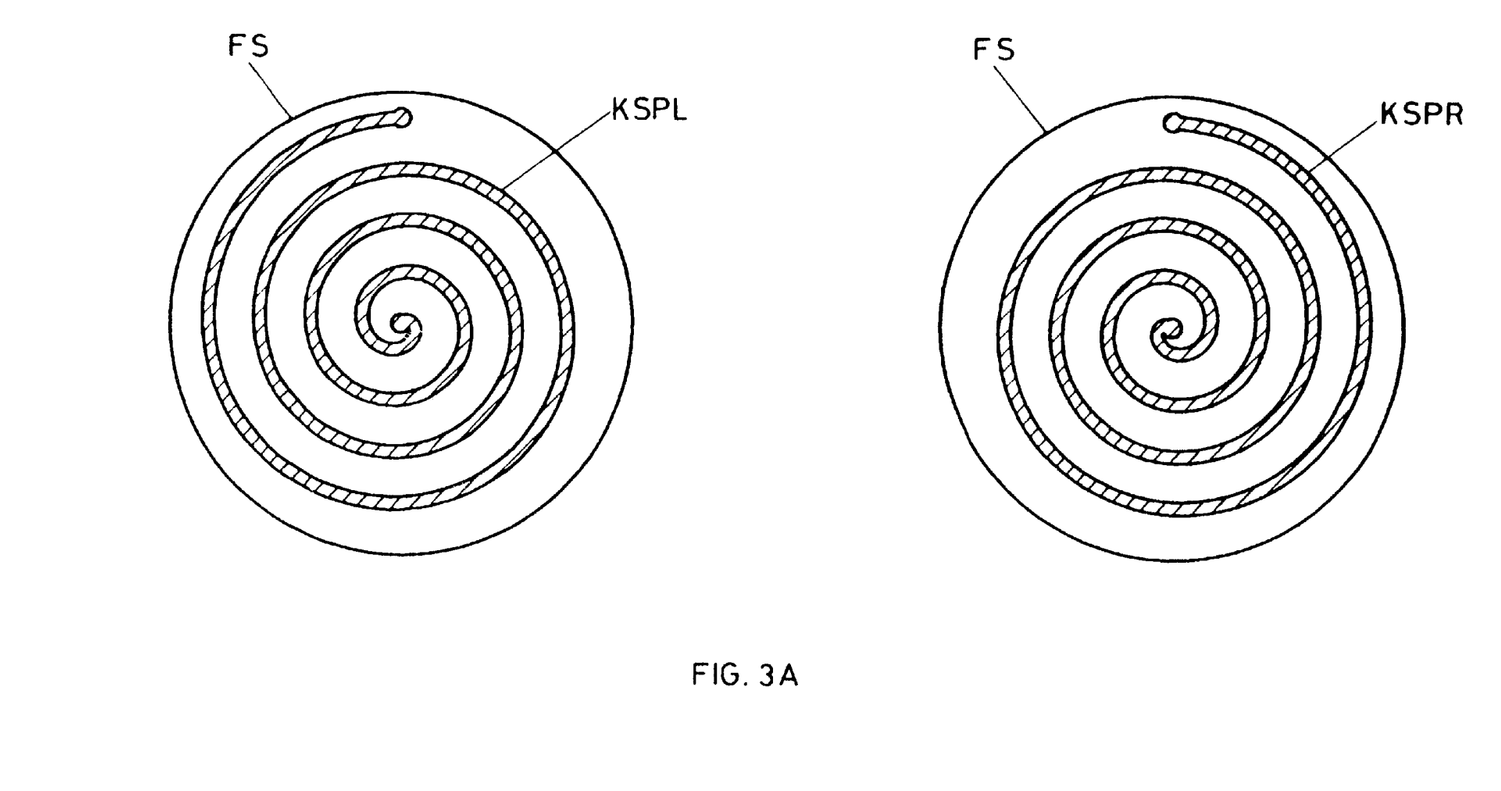
FIG. 3 shows another embodiment of the induction coil according to FIG. 2.
Figure 3B:
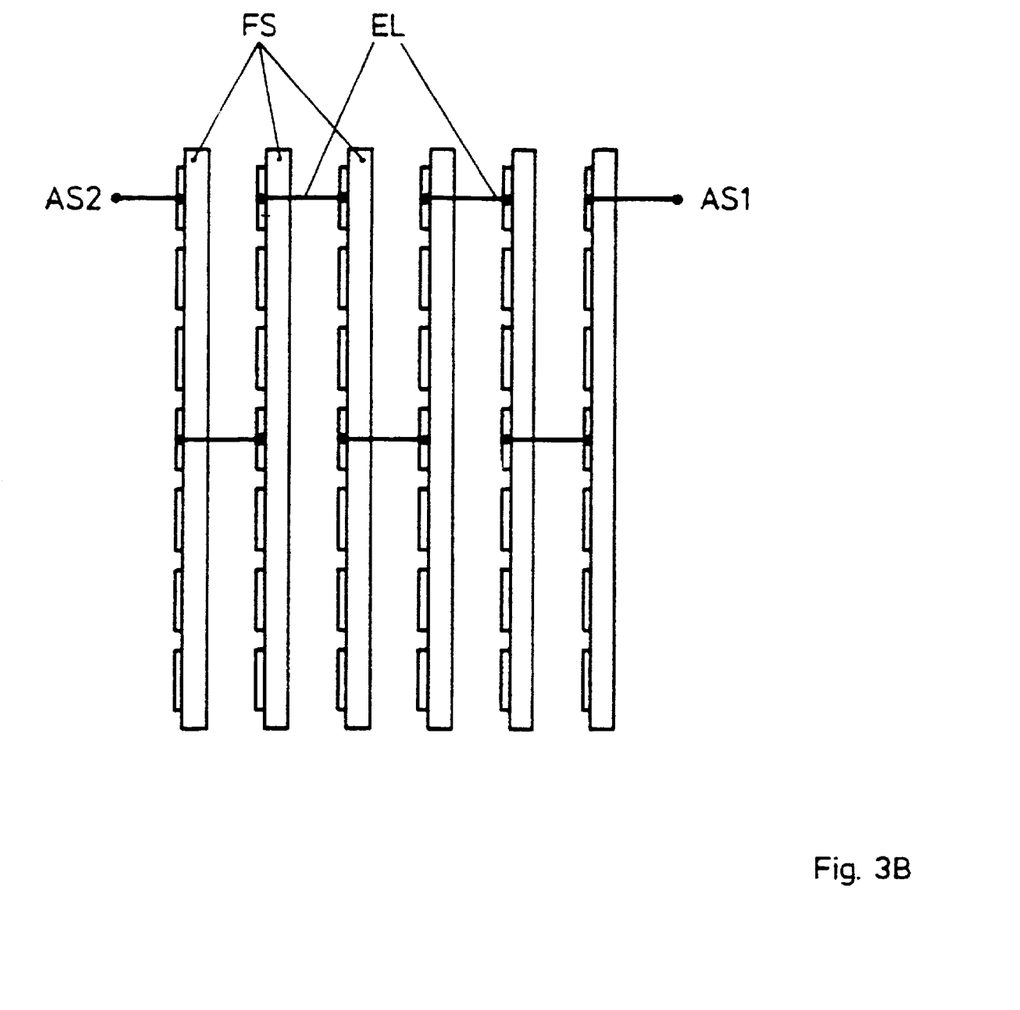

An important advantage of the induction coils explained in reference to FIG. 2C compared with the induction coils explained in reference to FIG. 2A is that additional electrical connecting lines between the winding start WA and the winding end WE are no longer required since all necessary connections are now located at the winding end WE (FIG. 2C). Another embodiment of the induction coils according to the invention is shown in FIG. 3, i.e., in FIGS. 3A and 3B, whereby the induction coils in this embodiment are constructed of foil plates FS onto which is applied by means of a photolithography process either a left-handed or a right-handed copper spiral KSPL or KSPR (FIG. 3A). Each of these left-handed copper spirals KSPL is connected via an electrical connecting line EL with a right-handed copper spiral KSPR at the internal spiral starting point. This has the result that the rotation direction of the copper strip does not change from the outside start of the left-handed spiral to the outside end of the right-handed spiral. This means that the induced signals are added. The induction coil is now constructed from such left-handed and right-handed spiral pairs according to the arrangement shown in FIG. 3B, whereby only the spiral pairs must be electrically connected on the outside.

The induction coils explained in reference to FIG. 2 and 3 can be used in any applications in which magnetic field components or their gradients must be determined. The mentioned induction coils are especially suitable as a gradiometer when, in particular, a high degree of accuracy of the values to be measured and a high sensitivity of the measuring unit is required. In addition, induction coils constructed in this manner literally suggest themselves for the determination of small magnetic field components or their gradients, since smaller values can be measured extremely accurately with these induction coils. A simple production of such induction coils furthermore ensures an exceedingly good reproducibility of the measuring values with various induction coils.

Since the induction coils used as receiver unit S11 to S22 react only to fields changing over time, the emitter coil constructed as emitter unit SE is excited with a time-variable current signal of known shape and size.

To form receiver unit S11 to S22, it is, however, also possible to use other sensors as induction coils. In particular, the use of SQUIDs is conceivable ("Sensors", W. Göpel et al. Verlag VC Hauer, Weinheim, 1989).

The position determination of an emitter unit SE by measuring the field modulated by it using gradiometers is not limited to the position determination of tumors to be irradiated. Rather, the device according to the invention can be used successfully anywhere where a contactless position determination is required.

In the explained embodiment version with an emitter unit at the object whose position is supposed to be determined, a further development is conceivable, i.e., that additional emitter units are placed with the respective object or at other sites. This makes it possible to determine several positions with the emitter units. Attention must however be paid to the fact that the emitter units are either sending in different periods of time (time multiplexing process) or with different frequencies (frequency multiplexing process).

In a similar manner, the embodiment version provided with a receiver unit in or near the object also can be developed further so that additional receiver units are provided in or near the object or at other sites. The advantage of this embodiment is that the positions of the different receiver units can be determined simultaneously since neither a time multiplexing nor a frequency multiplexing process is necessary.

The device according to the invention was explained in detail in reference to a medical application. The universality of the invention is however in no way limited by this. The device according to the invention is suitable in particular as a so-called three-dimensional mouse in "cyber space" applications, etc.

What is claimed is:

1. Device for determining a position of an object inside a space comprising:
   an emitter unit; and
   at least one pair of receiver units, each pair corresponding to a degree of freedom of the emitter unit, wherein the two receiver units of each pair are connected together to form a gradiometer;
   wherein the emitter unit is positioned as near as possible to the object inside the space.

2. Device of claim 1, further comprising an energy supply for supplying energy to at least one of the emitter unit and the at least two receiver units for each parameter.

3. Device of claim 2, wherein the energy supply is a generator unit the generator unit (GE) is in effective connection with the emitter unit or receiver unit positioned inside the space.

4. Device of claim 1, further comprising at least one calibration coil with a known position for calibrating the devise.

5. Device of claim 1, wherein the at least two receiver units for each parameter are constructed as induction coils, wherein the windings of the induction coils are constructed as parallel strips applied to a foil and are electrically conductive, and wherein ends of the parallel strips are connected via electrical connecting lines.

6. Device as claimed in claim 5, wherein the foil is folded twice in order to form two identical induction coils that are connected with each other.

7. Device as claimed in claim 1 wherein the at least two receiving units for each parameter are constructed as induction coils, wherein the induction coils comprise several foil plates, and electrically conductive spirals applied to the foil plates.

8. Device as claimed in claim 7, wherein some of the electrically conductive spirals have a right-handed spiral and others of the electrically conductive spirals have a left-handed spiral and the spirals are connected to form spiral pairs, wherein a spiral pair is formed by connecting electrically one of the electrically conductive spirals having a right-handed spiral and one of the electrically conductive spirals having a left-handed spiral with each other at the inside spiral end so as to form the spiral pair, and wherein the spiral pairs are connected with each other at the outside spiral end.

9. Device as claimed in claim 1, wherein the at least two receiver units for each parameter are constructed as magnetic field sensors.

10. Device of claim 9, wherein the magnetic field sensors are of the SQUID (Superconducting Quantum Interference Device) type.

11. Device as claimed in claim 1, further comprising:
   a signal conditioning unit; and
   a computation unit;
   wherein signals measured with the at least two receiver units for each parameter are conditioned in the signal conditioning unit, and the conditioned signals are evaluated in the computation unit to determine the position of the object.

12. Device of claim 1 further comprising an irradiation unit for irradiating the object.

13. Device of claim 12, wherein the irradiation unit tracks the object based on a determined position of the object.

14. Device of claim 13, wherein the irradiation unit is activated only when the object is located in a stationary target area.

15. Device of claim 12, wherein the irradiation unit is activated only when the determined position of the object is located in a stationary target area.

16. Device of claim 1, wherein the at least two receiver units for each parameter are located outside the space.

17. Device of claim 1, wherein the emitter unit is located inside the object.

18. Device of claim 1, wherein the object is a tumor located in a human body.

19. Device for determining a position of an object inside a space comprising:

at least one pair of emitter units, each pair corresponding to a degree of freedom of the receiver unit; and a receiver unit positioned as near as possible to the object;

wherein the two emitter units in each pair are connected together to generate a differential magnetic field.

20. Device of claim 19, wherein the at least two transmitter units for each parameter are located outside the space.

21. Device of claim 19, wherein the receiver unit is located inside the object.

22. Device of claim 19, wherein the object is a tumor located inside a human body.

23. Method for determining the position of an object in a space the method comprising the steps of:

positioning at least one emitter unit as close as possible to the object;

the at least one emitter unit generating an electromagnetic field;

measuring gradients of the generated electromagnetic field; and determining a position and an orientation of the at least one emitter unit based on the measured field gradients.

24. Method as claimed in claim 23 wherein the at least one emitter unit generates a differential electromagnetic field.

25. Method of claim 23 further comprising the steps of:

tracking the position of the object; and moving a target area to keep the object within the target area.

26. Method of claim 25, further comprising the step of irradiating the object only when the object is within the target area.

27. Method of claim 23, wherein the electromagnetic field is a magnetic field.

28. Method of claim 23, wherein the at least one emitter unit is positioned in the object.

29. Method of claim 23, wherein the object is a tumor in a human body.

30. Method for determining a position of an object in a space the method comprising the steps of:

positioning at least one receiver unit as close as possible to the object;

at least two emitter units located outside the space and generating a magnetic differential field;

the at least one receiver unit measuring the generated magnetic differential field, and determining a position of the at least one receiver unit based on the measurements of the at least one receiver unit.

31. Method of claim 30, wherein the at least one receiver unit is positioned within the object.

32. Method of claim 30, wherein the object is a tumor in a human body.

* * * * *